US011678897B2

(12) United States Patent
Cheng et al.

(10) Patent No.: US 11,678,897 B2
(45) Date of Patent: Jun. 20, 2023

(54) SURGICAL SYSTEM AND METHODS

(71) Applicant: MEDTRONIC INC., Minneapolis, MN (US)

(72) Inventors: Alan Cheng, Golden Valley, MN (US); Jian Cao, Shoreview, MN (US); Zhongping Yang, Woodbury, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 211 days.

(21) Appl. No.: 17/143,544

(22) Filed: Jan. 7, 2021

(65) Prior Publication Data

US 2022/0211401 A1 Jul. 7, 2022

(51) Int. Cl.
| | | |
|---|---|---|
| *A61B 17/22* | (2006.01) | |
| *A61N 1/05* | (2006.01) | |
| *A61N 7/00* | (2006.01) | |
| *A61N 1/39* | (2006.01) | |
| *A61M 25/09* | (2006.01) | |
| *A61N 1/362* | (2006.01) | |

(52) U.S. Cl.
CPC ...... *A61B 17/22012* (2013.01); *A61N 1/0573* (2013.01); *A61N 7/00* (2013.01); *A61B 2017/22014* (2013.01); *A61M 2025/09183* (2013.01); *A61N 1/362* (2013.01); *A61N 1/3956* (2013.01); *A61N 2007/0004* (2013.01); *A61N 2007/0047* (2013.01)

(58) Field of Classification Search
CPC .... A61B 17/22012; A61B 2017/22014; A61N 1/0573; A61N 7/00; A61N 1/362; A61N 1/3956; A61N 2007/0004; A61N 2007/0047; A61M 2025/09183
See application file for complete search history.

(56) References Cited

U.S. PATENT DOCUMENTS

| | | | |
|---|---|---|---|
| 7,829,029 B2 | 11/2010 | Zumeris et al. | |
| 9,028,748 B2 | 5/2015 | Zumeris et al. | |
| 10,328,268 B2 | 6/2019 | Sanghera et al. | |
| 2005/0038376 A1* | 2/2005 | Zumeris ............... | B08B 9/00 604/22 |
| 2005/0095351 A1* | 5/2005 | Zumeris ............... | A61L 2/24 427/2.1 |
| 2007/0239073 A1* | 10/2007 | Schaden ............... | A61N 7/00 601/2 |
| 2010/0233021 A1* | 9/2010 | Sliwa ................... | A61N 1/32 422/20 |
| 2019/0351226 A1 | 11/2019 | Echt et al. | |

FOREIGN PATENT DOCUMENTS

WO 2008011570 A1 1/2008

* cited by examiner

*Primary Examiner* — Hien N Nguyen
(74) *Attorney, Agent, or Firm* — Sorell, Lenna & Schmidt, LLP

(57) ABSTRACT

A surgical method treats infections on a lead positioned at least partially within a patient's body. The surgical method includes uncoupling the lead from a pulse generator. The lead is then coupled to an ultrasound wave generator. Ultrasound waves are propagated from the ultrasound wave generator through the lead. Systems are disclosed.

19 Claims, 15 Drawing Sheets

SURGICAL SYSTEM AND METHODS

TECHNICAL FIELD

The present disclosure generally relates to surgical systems and methods for the reduction and/or treatment of infections, and more particularly to surgical systems and methods for the treatment of infections on leads that are and are not coupled to implantable devices, wherein the infections are treated without removing the leads from the patient's body.

BACKGROUND

Infections of cardiac implantable electronic devices (CIEDs) are associated with high morbidity and mortality. Biofilm often builds up in or around indwelling leads of CIEDs. Fundamental to the perpetuation of CIED-related infections especially those involving the leads is the presence of bacteria-produced biofilm. In fact, biofilms are responsible for more than 80% of bacterial infections in humans. The buildup of biofilm on such leads limits the ability of systemic antibiotics to completely eradicate the infection. Studies have shown that ultrasonic energy can disrupt biofilm architecture and render bacteria more susceptible to the bactericidal activity of antibiotics.

Current approaches to CIED infection management involves complete system extraction, which at times is associated with an increased risk of death from the procedure. Indeed, current approaches to CIED infection management involve uncoupling one or more leads from within the patient (e.g., the patient's heart) and then removing the lead(s) from the patient's body. Once the infected lead(s) is/are removed from the patient's body, antibiotics are administered to the patient to cure the infection then the lead(s) may be replaced with one or more new leads.

It would therefore be useful to develop an approach that can destabilize the biofilm and therefore allow the antibiotics to effectively treat CIED infections, while avoiding complete system extraction. This disclosure thus describes improved systems and methods for the treatment of infections on leads that are and are not coupled to implantable devices, wherein the infections are treated without removing the leads from the patient's body.

SUMMARY

In one embodiment, in accordance with the principles of the present disclosure, a surgical method is provided for treating infections on a lead positioned at least partially within a patient's body. The surgical method comprises: uncoupling the lead from a pulse generator (if applicable); coupling the lead to an ultrasound wave generator; and propagating ultrasound waves from the ultrasound wave generator through the lead.

In some embodiments, the ultrasound waves are propagated through the lead to disrupt biofilm on the lead. In some embodiments, antibiotics are administered to the patient before, while and/or after the biofilm on the lead is disrupted by the ultrasound waves. In some embodiments, antibiotics are administered to the patient before the biofilm on the lead is disrupted by the ultrasound waves. In some embodiments, the ultrasound waves are propagated through the lead to disrupt biofilm on the lead, the surgical method further comprising administering antibiotics to the patient before propagating ultrasound waves from the ultrasound wave generator through the lead. In some embodiments, antibiotics are administered to the patient after the biofilm on the lead is disrupted by the ultrasound waves. In some embodiments, the lead is not removed from the patient before the surgical method is performed, while the surgical method is being performed, or after the surgical method is performed. In some embodiments, coupling the lead to the ultrasound wave generator comprises coupling a first end of the lead to the ultrasound wave generator while an opposite second end of the lead is coupled to the patient's heart. In some embodiments, the ultrasound waves are propagated through an inner coil of the lead to disrupt biofilm on the lead In one embodiment, in accordance with the principles of the present disclosure, a surgical method is provided for treating infections on a lead positioned at least partially within a patient's body. The surgical method comprises: creating an incision in the patient; creating a surgical pathway from the incision to the lead; inserting a guidewire into the incision and moving an end of the guidewire through the surgical pathway until the end is positioned adjacent to the lead; and propagating micro-vibration through the guidewire to disrupt biofilm on the lead.

In some embodiments, the guidewire is an ultrasonic transmission wire. In some embodiments, the guidewire is an ultrasonic angioplasty catheter. In some embodiments, the guidewire is a reverse piezoelectric guidewire. In some embodiments, the end of the guidewire is a first end of the guidewire, the guidewire comprising an opposite second end, the second end being connected to a power generator. In some embodiments, the method further comprises: uncoupling a first end of the lead from a pulse generator while an opposite second end of the lead is coupled to the patient's heart; and coupling the first end of the lead to an AC energy coupler, wherein the first end of the lead is coupled to the AC energy coupler as the micro-vibration is propagated through the guidewire.

In one embodiment, in accordance with the principles of the present disclosure, a surgical method for treating infections comprises: uncoupling a first end of a first lead from a pulse generator while an opposite second end of the first lead is coupled to a heart of a patient; uncoupling the second end of the first lead from the patient's heart; coupling a first end of a second lead to the patient's heart; coupling an opposite second end of the second lead to an energy source; and propagating energy from the energy source through the second lead to disrupt biofilm on the second lead.

In some embodiments, the second lead comprises an ultrasonic transducer positioned within a body of the second lead. In some embodiments, the ultrasonic transducer is directly coupled to an inner coil of the second lead. In some embodiments, the method further comprises administering antibiotics to the patient before and after propagating the energy from the energy source through the second lead. In some embodiments, the method further comprises: uncoupling second end of the second lead from the energy source; and coupling the second end of the second lead to the pulse generator

BRIEF DESCRIPTION OF THE DRAWINGS

The present disclosure will become more readily apparent from the specific description accompanied by the following drawings, in which.

Like reference numerals indicate similar parts throughout the figures.

DETAILED DESCRIPTION

Figure 1:
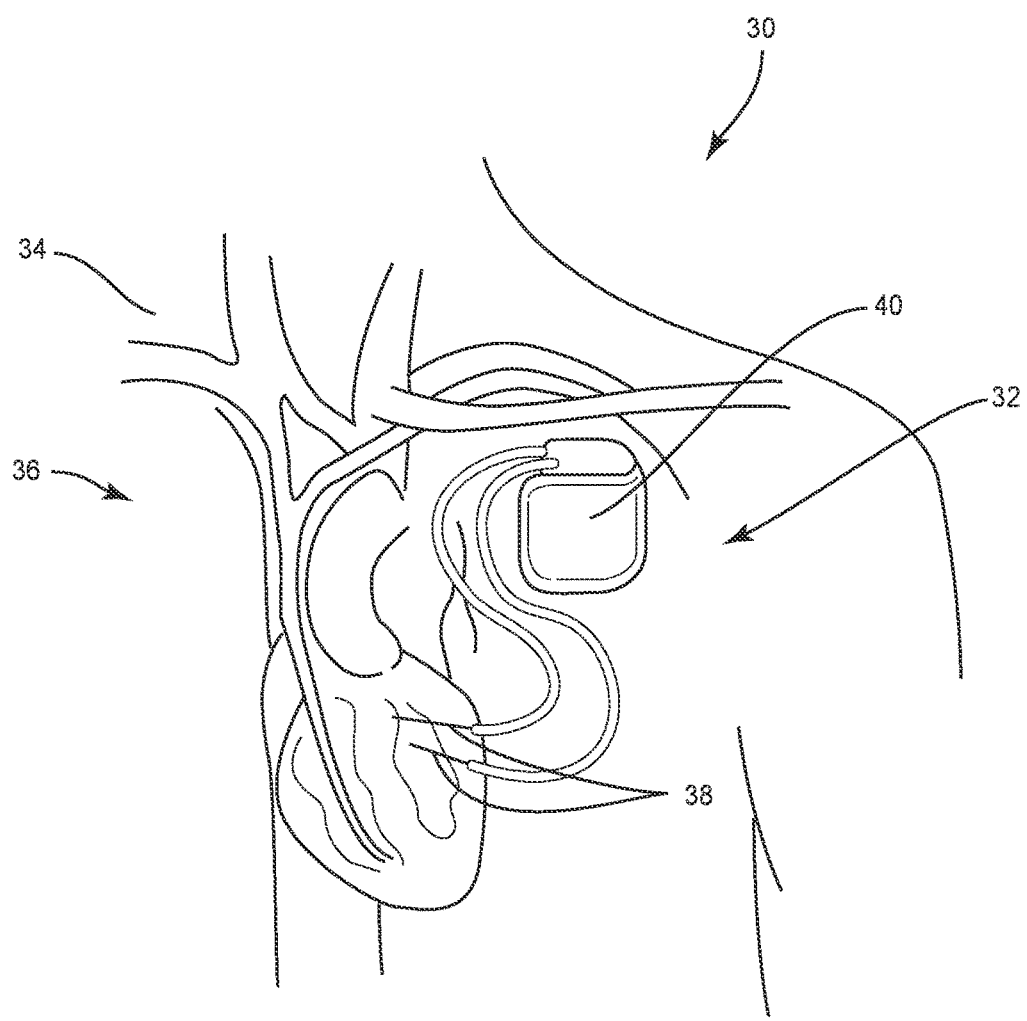
FIG. 1 is a plan view of components of a surgical system, in accordance with the principles of the present disclosure.
Figure 2:
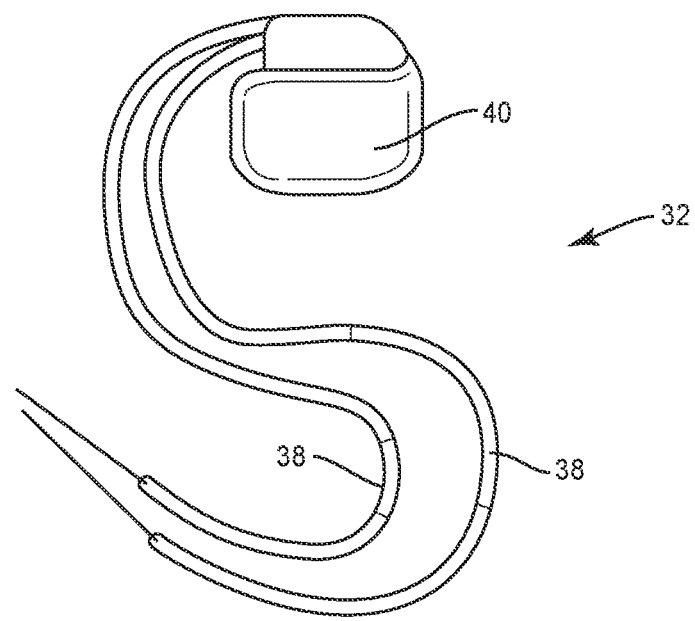
FIG. 2 is a perspective view of components of the surgical system shown in FIG. 1.
Figure 3:
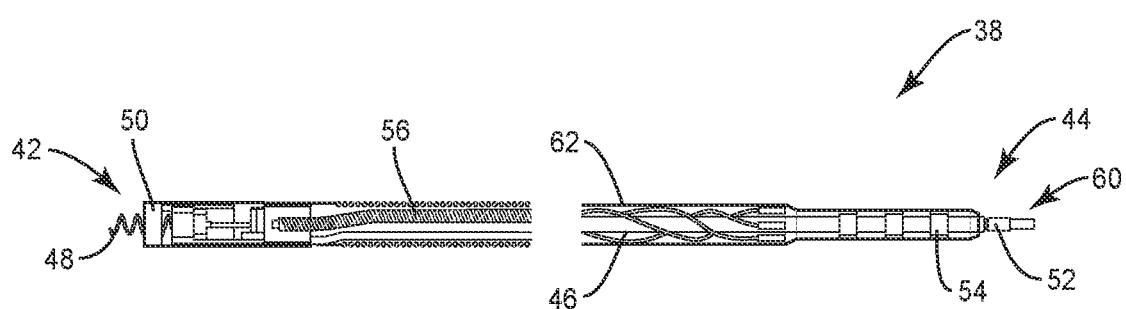
FIG. 3 is a side view, in part cross-section and in part phantom, of one embodiment of a component of the surgical system shown in FIG. 1, in accordance with the principles of the present disclosure.
Figure 4:
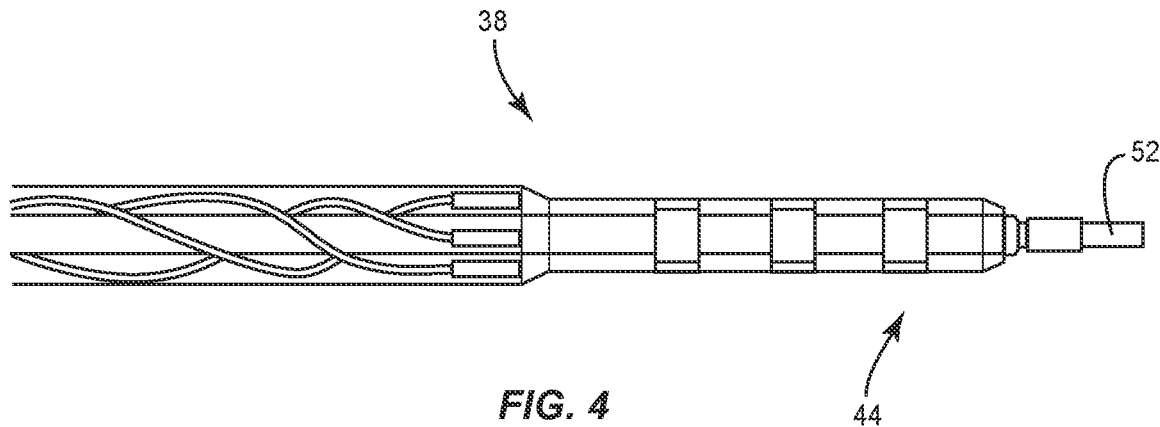
FIG. 4 is a side view, in part phantom, of a portion of one embodiment of a component of the surgical system shown in FIG. 1, in accordance with the principles of the present disclosure.
Figure 5:
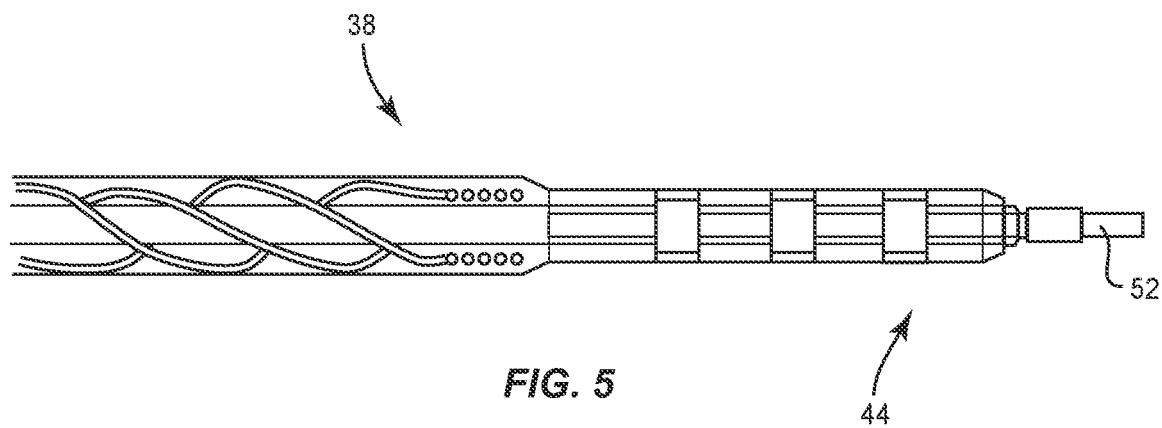
FIG. 5 is a side view, in part phantom, of a portion of one embodiment of a component of the surgical system shown in FIG. 1, in accordance with the principles of the present disclosure.
Figure 6:
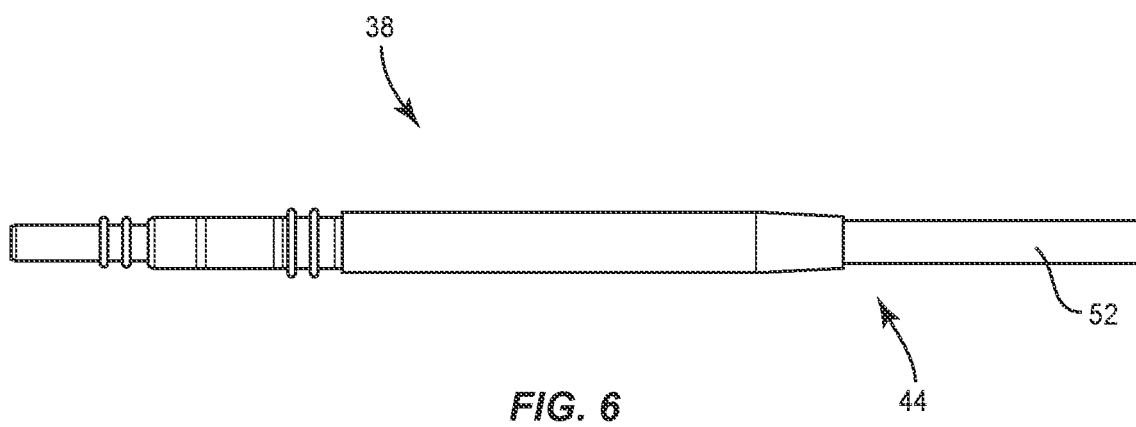
FIG. 6 is a side view, in part phantom, of a portion of one embodiment of a component of the surgical system shown in FIG. 1, in accordance with the principles of the present disclosure.
Figure 7:
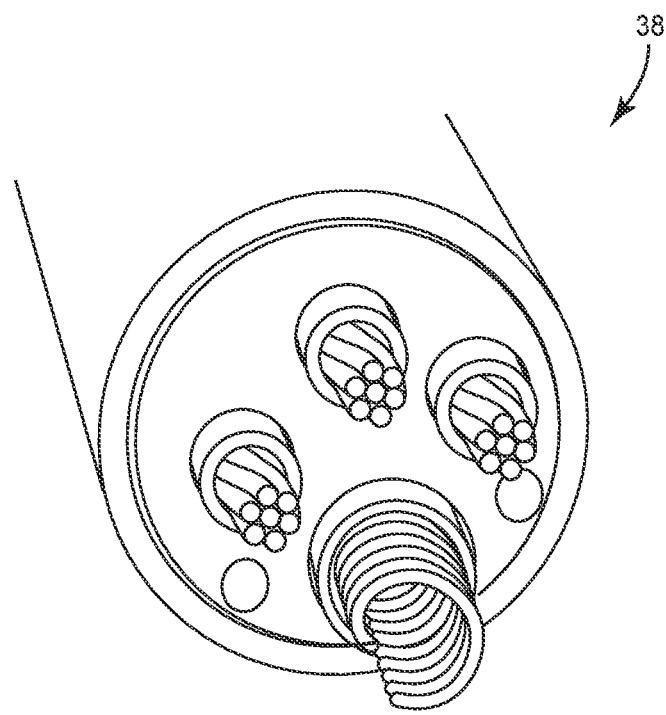
FIG. 7 is a perspective end view of one embodiment of a component of the surgical system shown in FIG. 1, in accordance with the principles of the present disclosure.
Figure 8:
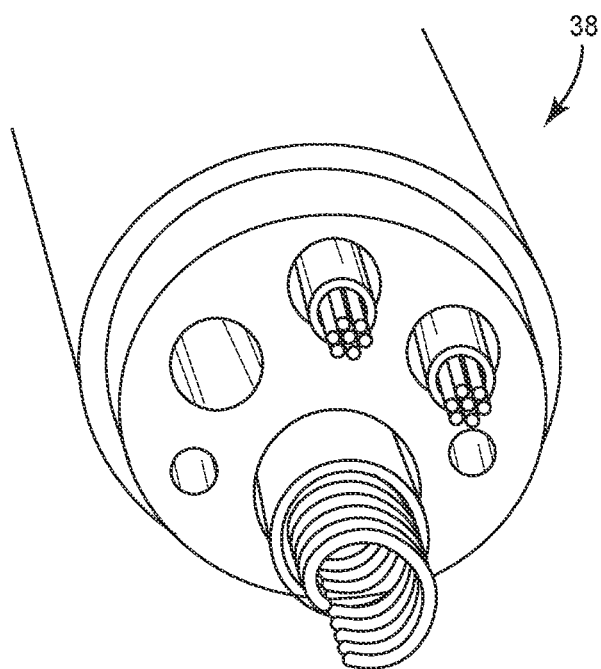
FIG. 8 is a perspective end view of one embodiment of a component of the surgical system shown in FIG. 1, in accordance with the principles of the present disclosure.
Figure 9:
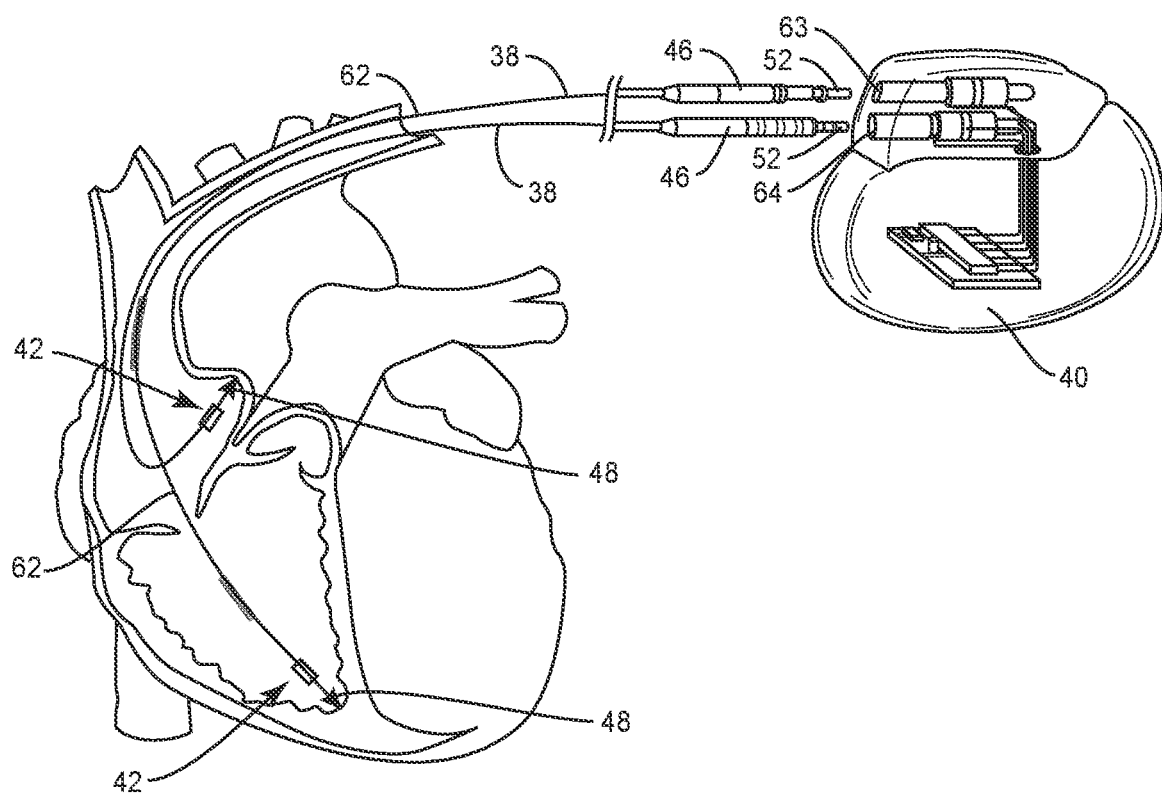
FIG. 9 is a plan view, in part phantom, of components of the surgical system shown in FIG. 1.
Figure 10:
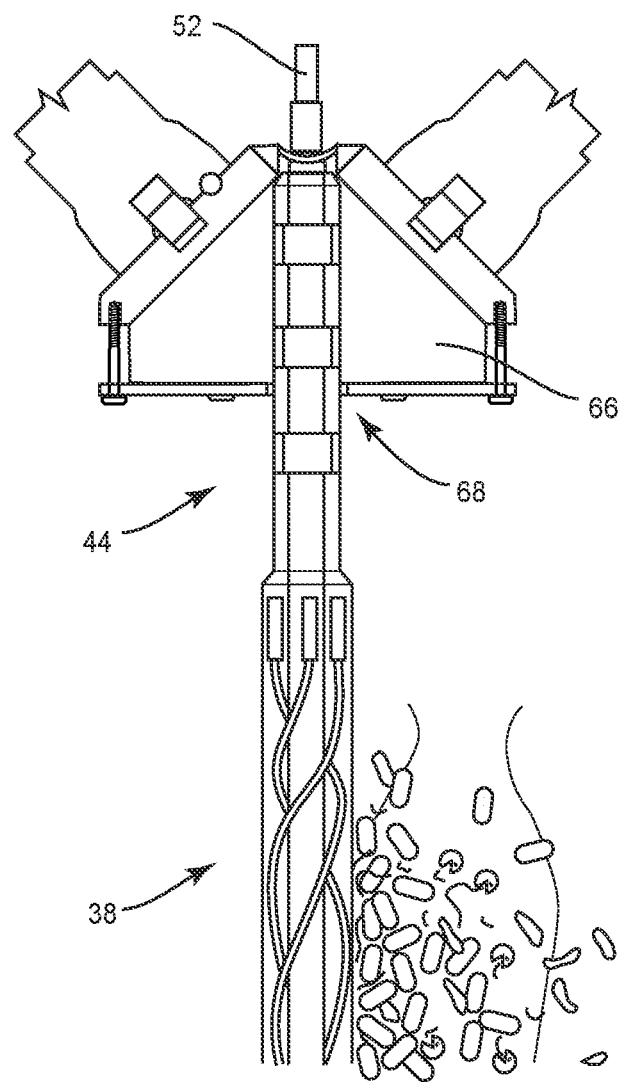
FIG. 10 is a plan view of components of the surgical system shown in FIG. 1.

The exemplary embodiments of the surgical system and related methods of use disclosed are discussed in terms of medical devices for the treatment and/or prevention of infections and more particularly, in terms of a surgical system and a method for the treatment of infections on leads that are coupled implantable devices, wherein the infections are treated without removing the leads from the patient's body. In some embodiments, the systems and methods of the present disclosure comprise medical devices including surgical instruments and implants that are employed with a surgical treatment, as described herein.

In some embodiments, the present surgical system and associated methods of the present disclosure utilize site-directed ultrasonic energy that is propagated through lead inner coil and transvenously delivered onto lead body to assist penetration of antibiotics into biofilm in presence of antibiotics in vivo. In particular, a minimally invasive approach is used to treat a pacemaker or defibrillator lead inflection, without removal of the lead. The minimally invasive approach comprises of an ultrasonic wave generator that can be coupled to a lead connector. The ultrasonic wave generator creates an ultrasonic wave that is propagated through an inner coil or fluid inside a body of the lead to disrupt the biofilm. Antibiotics are systemically administered simultaneously. The infection on the lead body is treated without removal of the lead body from the patient's body.

In some embodiments, the present surgical system and associated methods of the present disclosure includes a reverse piezoelectric guidewire that induces micro-vibration to enhance biofilm disruption and treat lead infection in the presence of antibiotics. In particular, a minimally invasive approach is used to treat a pacemaker or defibrillator lead inflection without removing the lead. The reverse piezoelectric guidewire delivers micro-vibration with AC energy to disrupt biofilm in or around the lead to enhance antibiotic penetration into biofilm while administering antibiotics in vivo. The infection on the lead body is treated without removal of the lead.

In some embodiments, the present surgical system and associated methods of the present disclosure includes an ultrasonic angioplasty catheter that breaks targeted encapsulated tissue/film to treat lead infection in the presence of antibiotics. In some embodiments, the method utilizes a minimally invasive procedure via a vein such that there is no need to open the pulse generator pocket.

In some embodiments, the present surgical system and associated methods of the present disclosure includes a lead having an ultrasonic transducer built into a body of the lead such that the ultrasonic transducer can deliver ultrasonic waves through a conductor cable of the lead to destabilize and/or disrupt biofilm on an outer surface of the lead body.

In some embodiments, the present surgical system and associated methods of the present disclosure may be employed with a patient in a prone or supine position, and/or employ various surgical approaches, including anterior, posterior, posterior mid-line, direct lateral, postero-lateral, and/or antero-lateral approaches, and in other body regions. The surgical system and associated methods of the present disclosure may also be used on animals, bone models and other non-living substrates, such as, for example, in training, testing and demonstration.

The surgical system and associated methods of the present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease, infection or other condition refers to performing a procedure that may include administering one or more drugs to a patient (human, normal or otherwise or other mammal), employing implantable devices, and/or employing instruments that treat the disease. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. In some embodiments, as used in the specification and including the appended claims, the term "tissue" includes soft tissue, ligaments, tendons, cartilage and/or bone unless specifically referred to otherwise.

The following discussion includes a description of a surgical system including implants, related components and methods of employing the surgical system in accordance with the principles of the present disclosure. Alternate embodiments are also disclosed. Reference is made in detail to the exemplary embodiments of a surgical system 30, which are illustrated in the accompanying figures.

The components of surgical system 30 can be fabricated from biocompatible materials suitable for medical applications, including metals, synthetic polymers, ceramics and bone material and/or their composites. For example, the components of surgical system 30, individually or collectively, can be fabricated from materials such as stainless steel alloys, aluminum, commercially pure titanium, titanium alloys, Grade 5 titanium, super-elastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of surgical system 30 may have material composites, including the above materials, to achieve various desired characteristics such as strength, rigidity, elasticity, compliance, biomechanical performance, durability and radiolucency or imaging preference. The components of surgical system 30, individually or collectively, may also be fabricated from a heterogeneous material such as a combination of two or more of the above-described materials. The components of surgical system 30 may be monolithically formed, integrally connected or include fastening elements and/or instruments, as described herein.

Surgical system 30 includes an implantable medical device 32 that is configured to be implanted within a body 34 of a patient 36. In some embodiments, device 32 is an implantable electronic device, such as, for example, a pacemaker. Device 32 may be implanted in patient 36 using any procedure known in the art.

In one embodiment, device 32 is implanted into patient 36 using an endocardial (transvenous) approach. A local anesthetic is given to numb at least a portion of patient 36, such as, for example, the chest of patient 36. An incision is made in the chest of patient 36. One or more leads 38 of device 32 and a pulse generator 40 are inserted through the incision. Leads 38 are each inserted into a vein of patient 36. Leads 38 are then guided through the veins of patient 36 until ends 42 of leads 38 are positioned adjacent to the heart of patient 36. In some embodiments, leads 38 are guided through the veins of patient 36 with the aid of a fluoroscopy machine. Ends 42 are then attached to the heart of patient 36. Opposite ends 44 of leads 38 are then coupled to pulse generator 40. In some embodiments, ends 44 and/or pulse generator 40 are placed in a pocket created under the skin of patient 36 in the upper chest of patient 36 to secure pulse generator 40 within patient 36.

In one embodiment, device 32 is implanted into patient 36 using an epicardial approach. Patient 36 is administered general anesthesia. Ends 42 are attached to the heart of patient 36, while ends 44 are attached to pulse generator 40, wherein ends 44 and/or pulse generator 40 are placed in a pocket created under the skin in the abdomen.

In some embodiments, lead 38 includes a body 46. A fixation screw 48 extends outwardly from an end 50 of body 46. Screw 48 is configured to be inserted directly into heart tissue of patient 36. A connector 52 extends outwardly from an opposite end 54 of body 46. A coil 56 extends from connector 52 to a wire 58 that is coupled to screw 48 such that electrical pulses generated by pulse generator 40 move through connector 52, coil 56, wire 58 and screw 48 and into the heart of patient 36 to control heartrate. In some embodiments, connector 52 is coupled directly to pulse generator 40 by inserting an end 60 of connector 52 into a corresponding socket of pulse generator 40, for example.

Over time (days, week, months, etc.), infectious biofilms may form on and/or around leads 38. For example, such biofilms may form on and/or around an outer surface 62 of body 46. The biofilm on and/or around outer surface 62 must be disrupted in order to render bacteria that form the biofilm more susceptible to the bactericidal activity of antibiotics. To disrupt the biofilm on and/or around outer surface 62 without disengaging screw 48 from the heart of patient 36, an incision is made in the patient and a surgical pathway is created from the incision to pulse generator 40. End 44 is uncoupled from pulse generator 40 by removing connector 52 from a socket 63 of pulse generator 40 or a socket 64 of pulse generator 40, for example. After being removed from socket 63 or socket 64, end 44 is coupled to an ultrasound wave generator 66 by inserting connector 52 into a socket 68 of ultrasound wave generator 66. Ultrasound wave generator 66 is then turned from an off position to an on position, for example, such that ultrasound wave generator 66 propagates ultrasound waves that move through lead 38. As the ultrasound waves move along the length of lead 38, the ultrasound waves cause lead 38 to vibrate such that biofilm on and/or around outer surface 62 is disrupted. In some embodiments, ultrasound wave generator 66 is configured to generate high energy ultrasound. In some embodiments, ultrasound wave generator 66 is configured to generate high energy ultrasound with a frequency of about 20 Khz.

It is envisioned that system 30 may include and that the associated methods of use discussed herein may be used with any type of implantable electronic device, such as, for example, cardiac implantable electronic devices (e.g., pacemakers and defibrillators), as well as other types of implantable electronic devices. It is further envisioned that system 30 may include and that the associated methods of use discussed herein may be used with any type of leads that are conventionally used with conventional implantable electronic devices. That is, the implantable electronic devices and corresponding leads of system 30 are standard, off the shelf components that need not be modified in order to be used in connection with the associated methods of use discussed herein. Examples of such standard, off the shelf components are shown in FIGS. 2-8. As would be recognized by one of ordinary skill in the art, system 30 may include and the associated methods of use discussed herein may be used with all variations of implantable electronic devices. For example, system 30 may include and the associated methods of use discussed herein may be used with implantable electronic devices having one or a plurality of leads wherein the leads may be the same or different when a plurality of leads are included.

Figure 11:
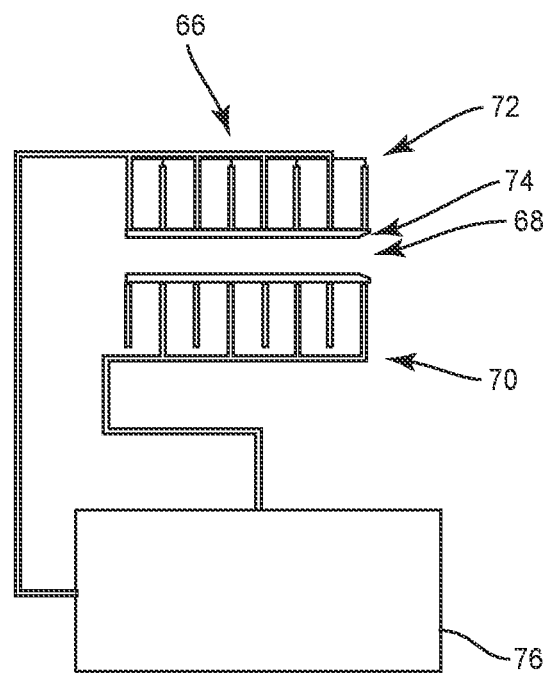
FIG. 11 is a schematic view of components of the surgical system shown in FIG. 1.
Figure 12:
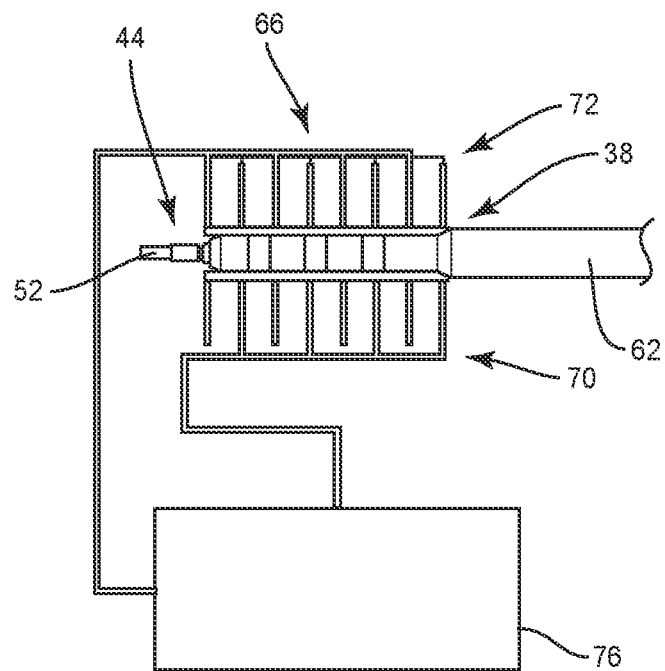
FIG. 12 is a schematic view of components of the surgical system shown in FIG. 1.
Figure 13:
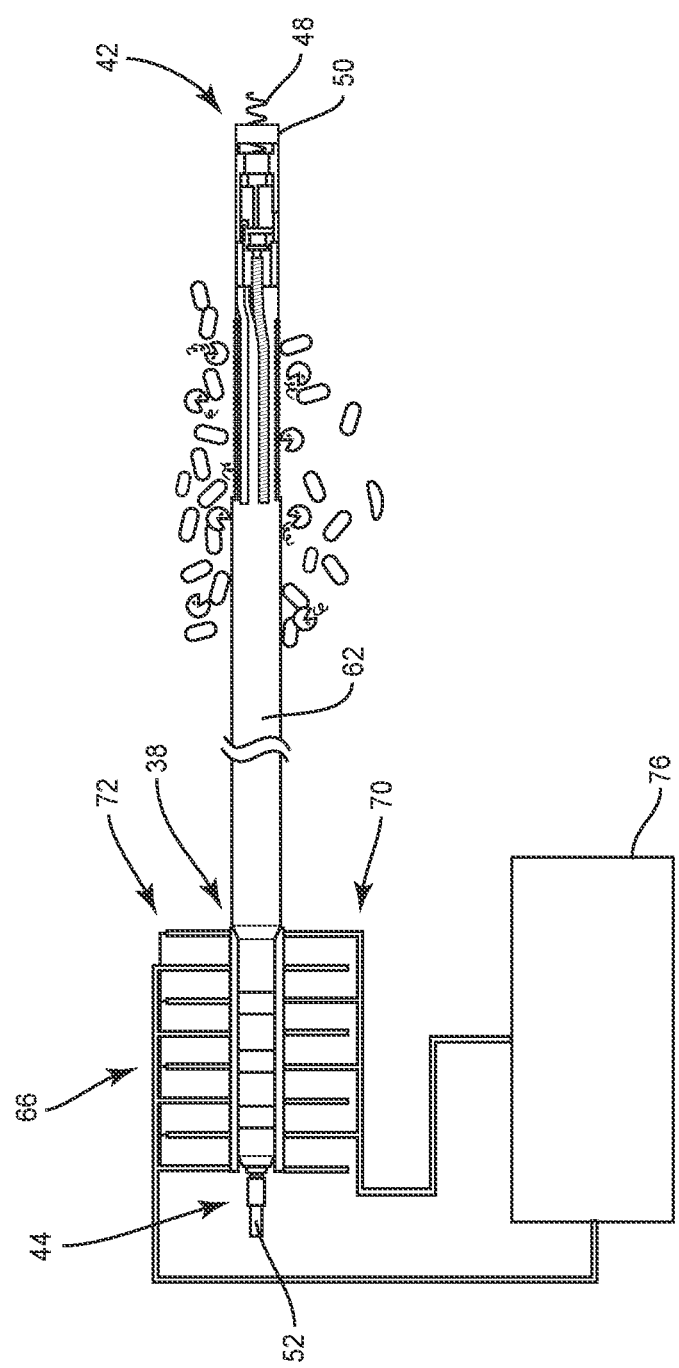
FIG. 13 is a schematic view of components of the surgical system shown in FIG. 1.
Figure 14:
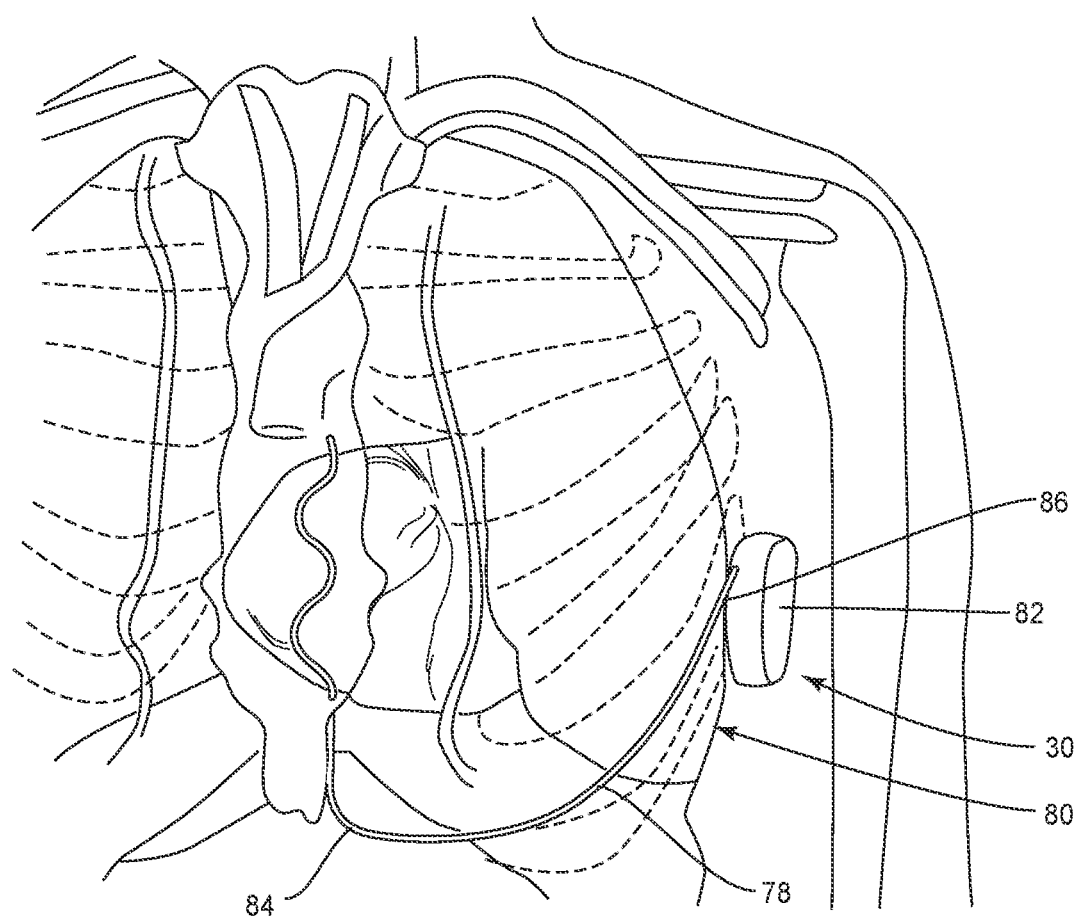
FIG. 14 is a plan view of components of a surgical system, in accordance with the principles of the present disclosure.
Figure 15:
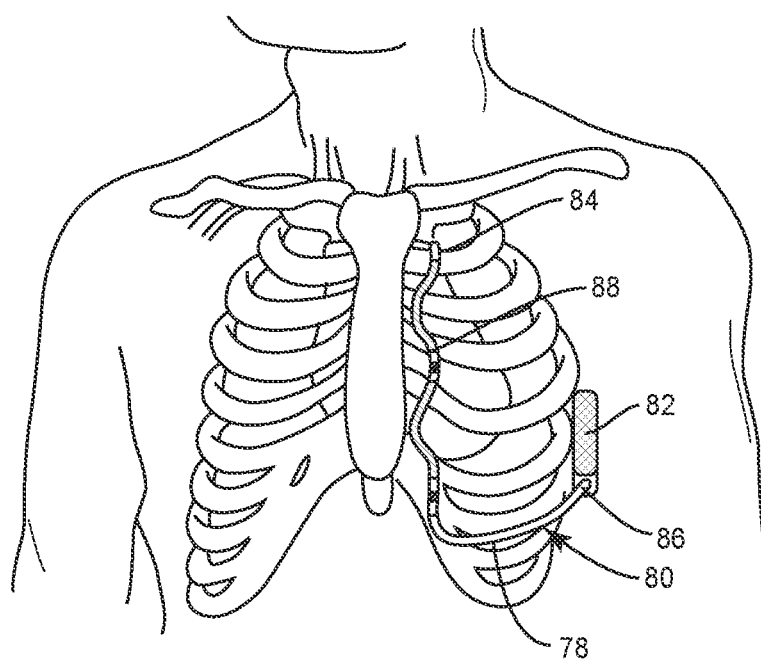
FIG. 15 is a plan view of components of the surgical system shown in FIG. 14.
Figure 16:
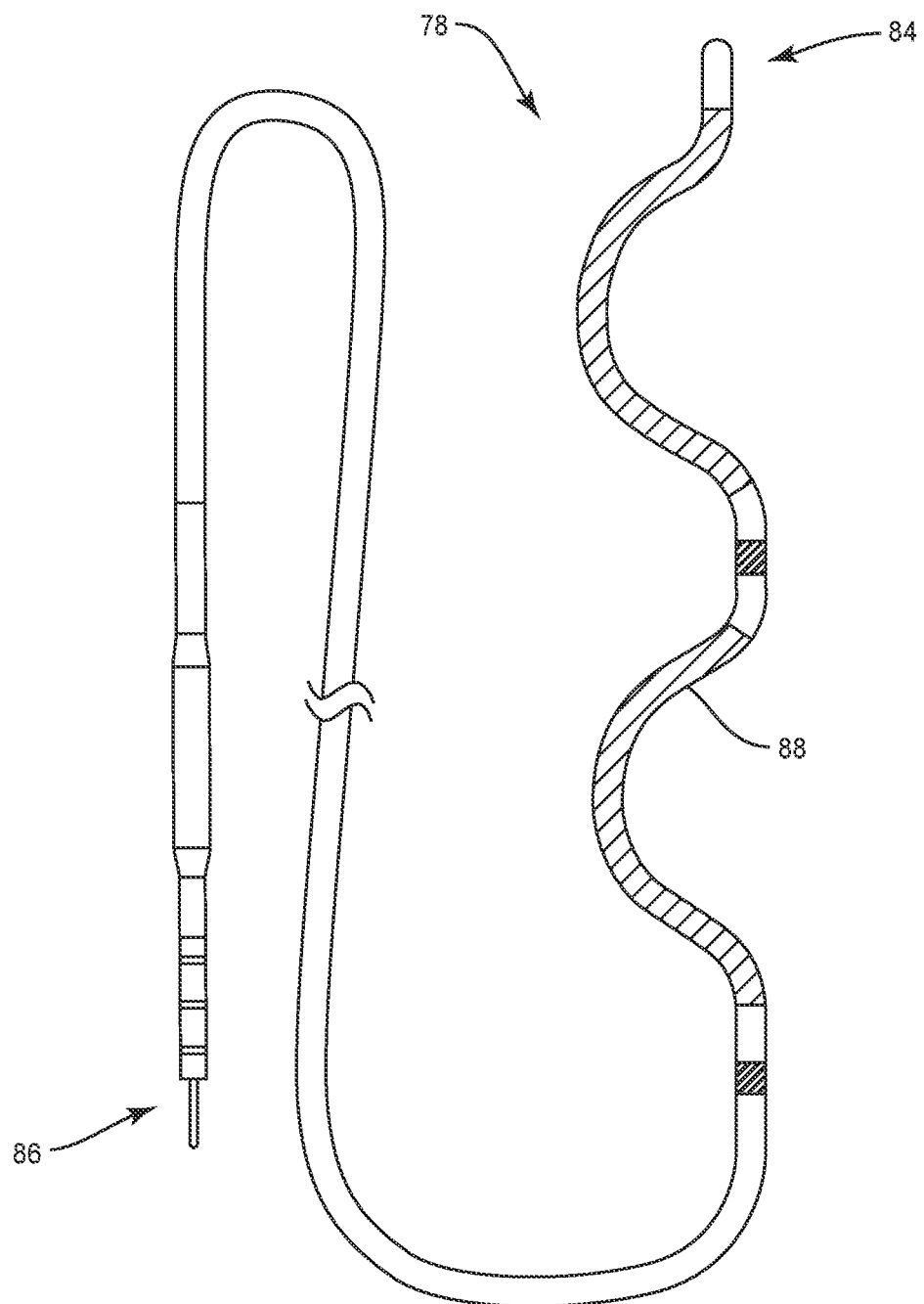
FIG. 16 is a perspective view of a component of the surgical system shown in FIG. 14.
Figure 17:
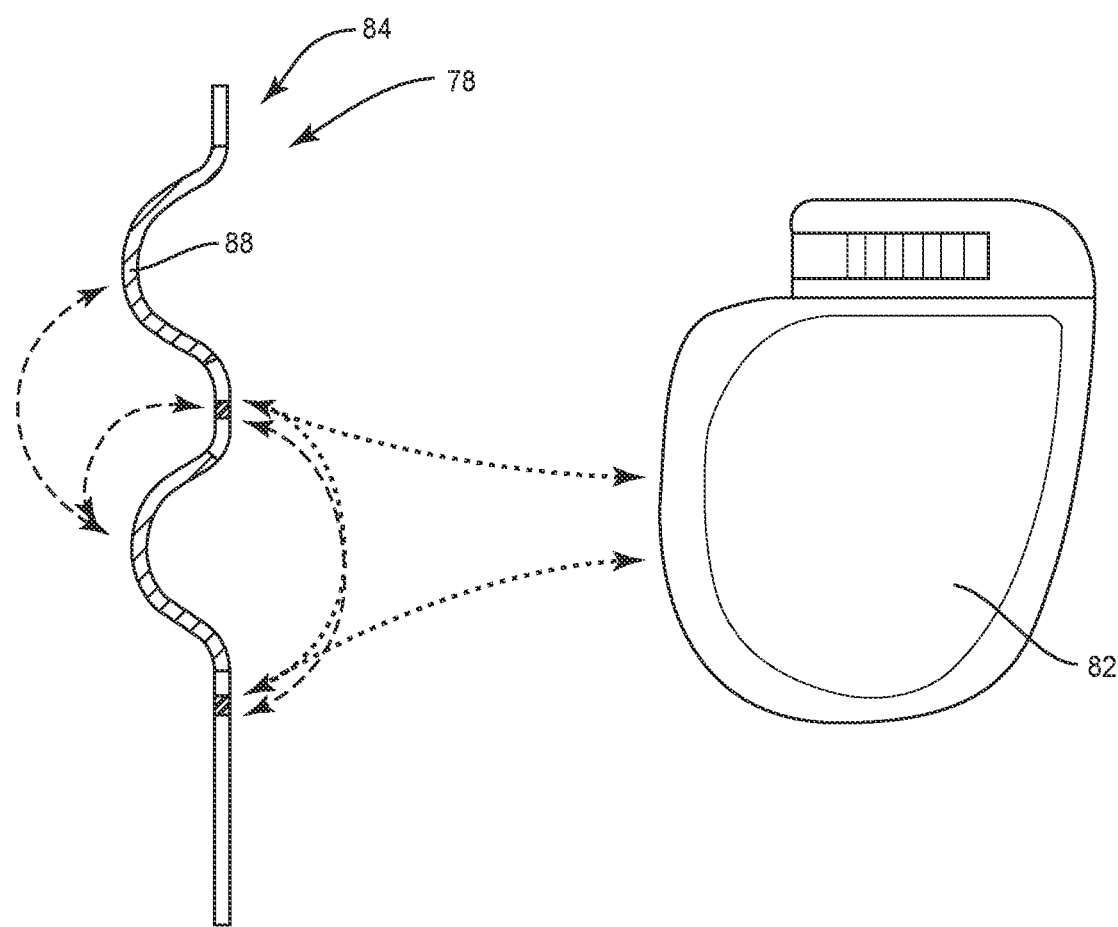
FIG. 17 is a perspective view of components of the surgical system shown in FIG. 14.
Figure 18:
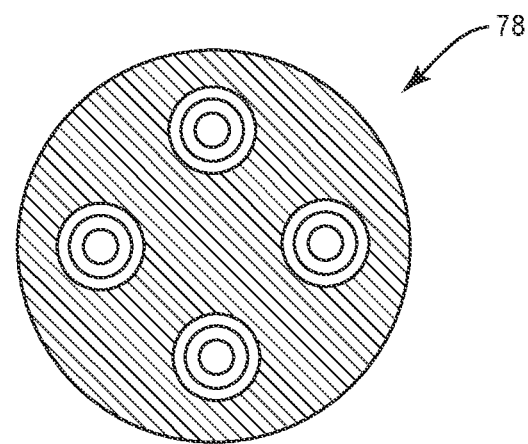
FIG. 18 is a cross-sectional view of a component of the surgical system shown in FIG. 14.

In some embodiments, shown in FIGS. 11-13, ultrasound wave generator 66 includes an electrode 70 having a piezoelectric disc 72, such as, polyvinylidene fluoride film, quartz, ammonium dihydrogen phosphate crystal, that defines socket 68. In some embodiments, inner surfaces of disc 72 are coated with an insulator, such as, for example, a PTFE polymer insulator. Ultrasound wave generator 66 further includes a power supplier, such as, for example, a power source 76 (Power: 5 W up to 200 W, Frequency: 20-60 kHz).

In some embodiments, antibiotics are simultaneously administered to the patient while the biofilm on and/or around outer surface 62 of lead 38 is disrupted by the ultrasound waves. In some embodiments, antibiotics are administered to the patient before the biofilm on and/or around outer surface 62 of lead 38 is disrupted by the ultrasound waves. That is, the antibiotics may be administered to the patient before lead 38 is uncoupled from pulse generator 40. In some embodiments, antibiotics are administered to the patient before and/or after the biofilm on and/or around outer surface 62 of lead 38 is disrupted by the ultrasound waves. In some embodiments, the antibiotics are administered systemically and/or locally. In some embodiments, end 42 remains coupled to the patient's heart before the surgical method is performed, while the surgical method is being performed, or after the surgical method is performed. That is, end 42 remains coupled to the patient's heart before lead 38 is uncoupled from pulse generator 40, while lead 38 is being coupled to ultrasonic wave generator and while ultrasound wave generator 66 propagates ultrasound waves that move through lead 38. In some embodiments, the ultrasound waves are propagated through coil 56.

Upon completion of a procedure, as described herein, the surgical instruments, assemblies and non-implanted components of surgical system 30 are removed and the incision(s) are closed. One or more of the components surgical system 30 can be made of radiolucent materials such as polymers. Radiomarkers may be included for identification under x-ray, fluoroscopy, CT or other imaging techniques.

It is envisioned that that the method discussed in the preceding paragraphs may be used in connection with the treatment of one or more leads 78 of an extravascular implantable cardioverter defibrillator 80, as shown in FIGS. 14-18. In particular, defibrillator 80 is implanted into a patient. A local anesthetic is given to numb at least a portion of the patient, such as, for example, the chest of the patient. An incision is made in the chest of the patient. One or more leads 78 of defibrillator 80 and a pulse generator 40 are inserted through the incision and lead 78 is placed outside of the patient's heart and veins. An end 84 is attached to the patient's anatomy and an opposite end 86 of lead 78 is coupled to pulse generator 82.

Over time (days, week, months, etc.), infectious biofilms may form on and/or around lead 78. For example, such biofilms may form on and/or around an outer surface 88 of lead 78. The biofilm on and/or around outer surface 88 must be disrupted in order to render bacteria that form the biofilm more susceptible to the bactericidal activity of antibiotics. To disrupt the biofilm on and/or around outer surface 88 without uncoupling end 84 from the patient's anatomy, an incision is made in the patient and a surgical pathway is created from the incision to pulse generator 82. End 86 is uncoupled from pulse generator 82. End 86 is then coupled to an ultrasound wave generator, such as, for example, ultrasound wave generator 66 by inserting end 86 into socket 68 of ultrasound wave generator 66. Ultrasound wave generator 66 is then turned from the off position to the on position, for example, such that ultrasound wave generator 66 propagates ultrasound waves that move through lead 78. As the ultrasound waves move along the length of lead 78, the ultrasound waves cause lead 78 to vibrate such that biofilm on and/or around outer surface 88 is disrupted.

In some embodiments, antibiotics are simultaneously administered to the patient while the biofilm on and/or around outer surface 88 of lead 78 is disrupted by the ultrasound waves. In some embodiments, antibiotics are administered to the patient before the biofilm on and/or around outer surface 88 of lead 78 is disrupted by the ultrasound waves. That is, the antibiotics may be administered to the patient before lead 78 is uncoupled from pulse generator 82. In some embodiments, antibiotics are administered to the patient before and/or after the biofilm on and/or around outer surface 88 of lead 78 is disrupted by the ultrasound waves. In some embodiments, the antibiotics are administered systemically and/or locally. In some embodiments, end 84 remains coupled to the patient before the surgical method is performed, while the surgical method is being performed, or after the surgical method is performed.

That is, end 84 remains coupled to the patient before lead 78 is uncoupled from pulse generator 82, while lead 78 is being coupled to ultrasonic wave generator 66 and while ultrasound wave generator 66 propagates ultrasound waves that move through lead 78.

Upon completion of a procedure, as described herein, the surgical instruments, assemblies and non-implanted components of surgical system 30 are removed and the incision(s) are closed. One or more of the components surgical system 30 can be made of radiolucent materials such as polymers. Radiomarkers may be included for identification under x-ray, fluoroscopy, CT or other imaging techniques.

Figure 19:
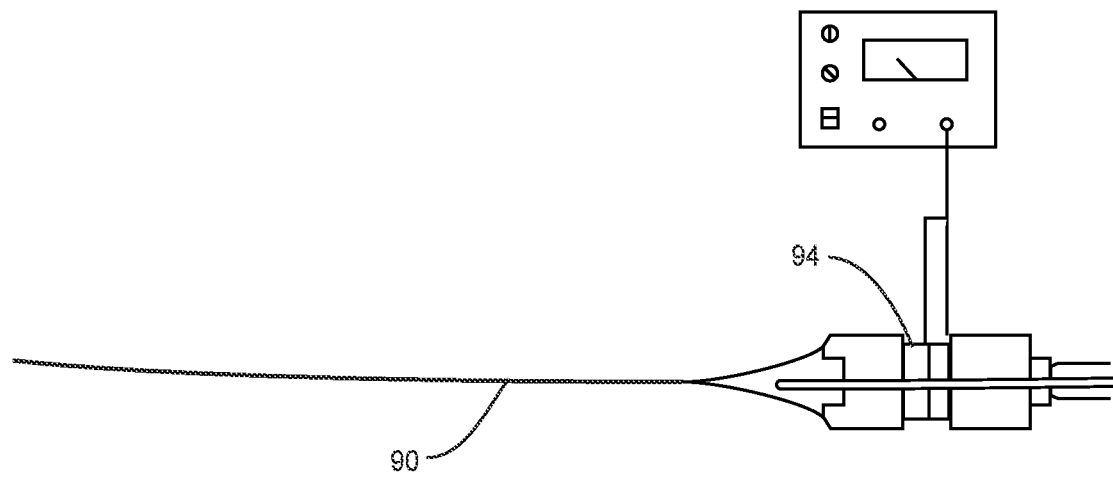
FIG. 19 is a side view of components of a surgical system, in accordance with the principles of the present disclosure.
Figure 20:
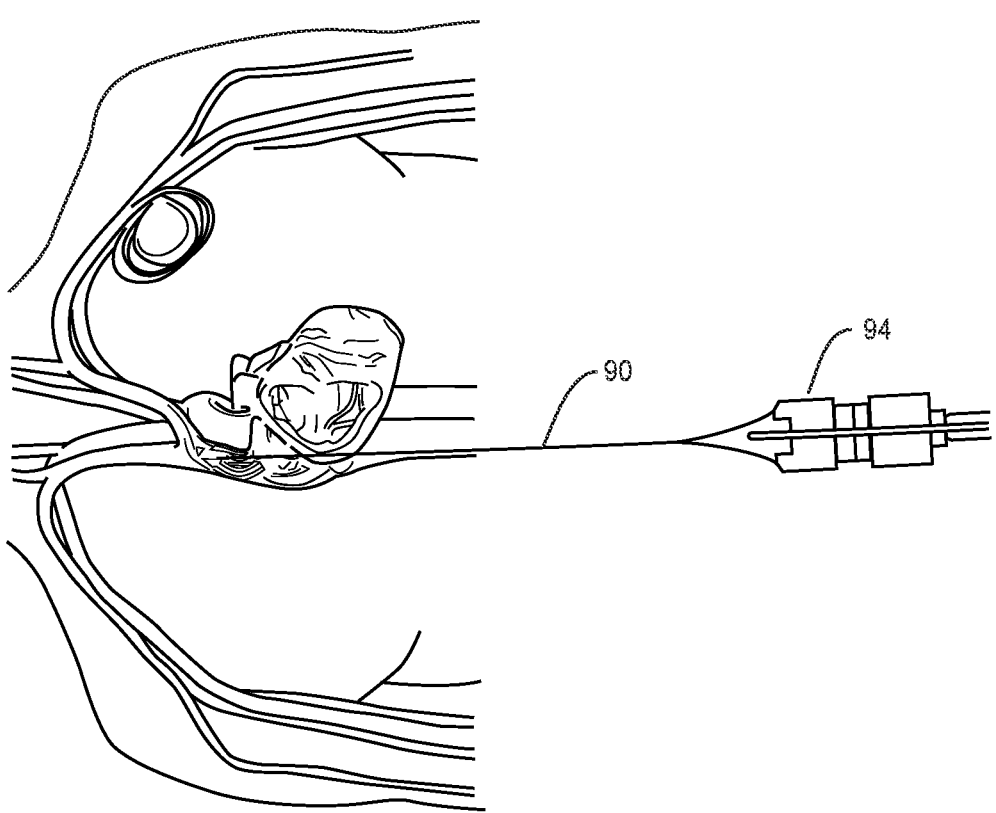
FIG. 20 is a plan view of components of the surgical system shown in FIG. 19.

In some embodiments, a method is disclosed, which does not use an ultrasound wave generator, such as, for example, ultrasound wave generator 66. Rather, one method uses a guidewire, such as, for example, an ultrasonic transmission wire 90 to disrupt biofilm on and/or around outer surface 62 or outer surface 88. In particular, an incision is made in the patient and a surgical pathway is created from the incision to lead 38 or lead 78. In some embodiments, the surgical pathway does not extend into a pocket in which pulse generator 40 or pulse generator 82 is disposed within the patient's body and/or to pulse generator 40 or pulse generator 82. Ultrasonic transmission wire 90 is guided through the surgical pathway until an end 92 of ultrasonic transmission wire 90 is positioned adjacent to outer surface 62 or outer surface 88. In some embodiments, end 92 directly engages outer surface 62 or outer surface 88. In some embodiments, end 92 is spaced apart from outer surface 62 or outer surface 88 at all times. A power generator 92 provides power to a piezoelectric element 94 (FIG. 19), which propagates ultrasound waves that move through ultrasonic transmission wire 90. The ultrasound waves cause ultrasonic transmission wire 90 to vibrate such that the vibration of ultrasonic transmission wire 90 disrupts biofilm on and/or around outer surface 62 or outer surface 88. Ultrasonic transmission wire 90 may be moved along the length of lead 38 or lead 78 and/or radially about lead 38 or lead 78 until the desired amount of biofilm is disrupted.

Upon completion of a procedure, as described herein, the surgical instruments, assemblies and non-implanted components of surgical system 30 are removed and the incision(s) are closed. One or more of the components surgical system 30 can be made of radiolucent materials such as polymers. Radiomarkers may be included for identification under x-ray, fluoroscopy, CT or other imaging techniques.

Figure 21:
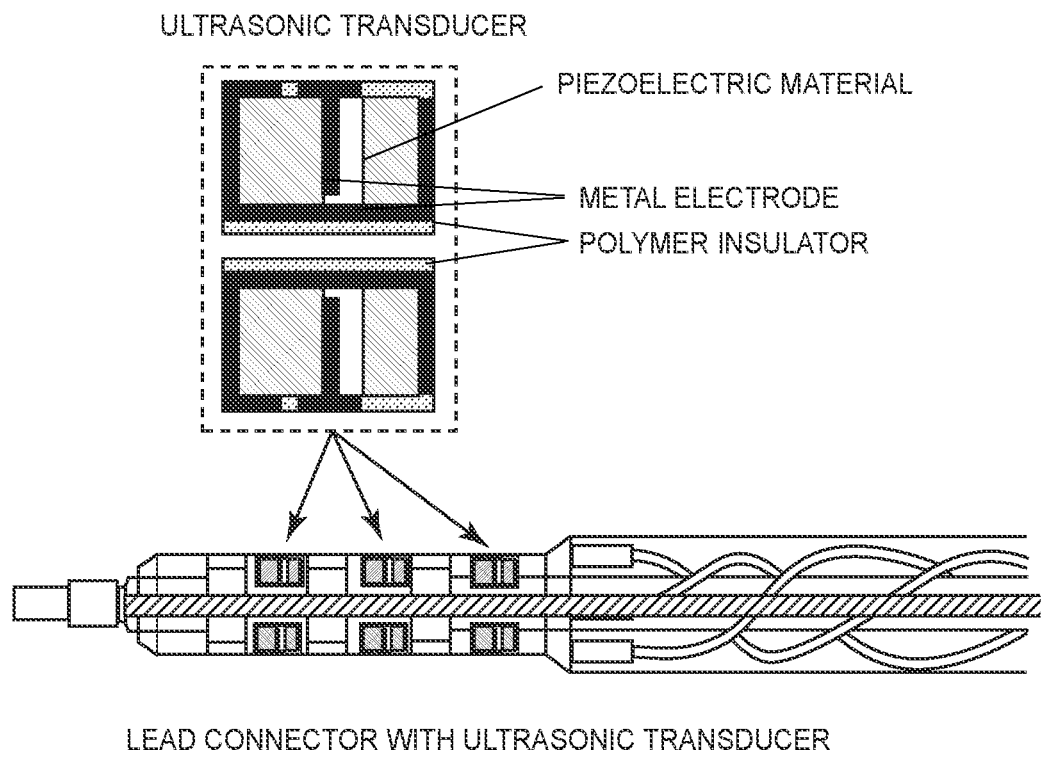
FIG. 21 is a side view, in part cross-section, of a component of a surgical system, in accordance with the principles of the present disclosure.
Figure 22:
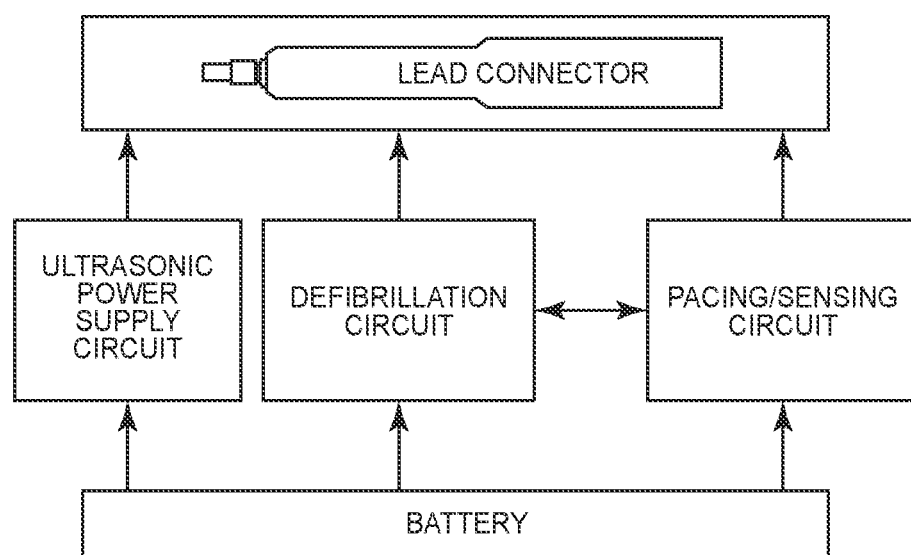
FIG. 22 is a diagram showing features of the component shown in FIG. 21.

In one embodiment, a novel lead 96 (FIG. 21) includes an ultrasonic transducer 98 incorporated within a body 100 of lead 96. Transducer 98 includes spaced apart elements 99, wherein elements 99 each include piezoelectric material 101, a metal electrode 103 and a polymer insulator.

In some embodiments, lead(s) 96 may be used to replace existing leads of an implantable electronic device, such as, for example, lead 38 or lead 78. For example, when biofilm builds up on or around outer surface 62 of lead 38, a surgical pathway is created from an incision to screw 48 to allow screw 48 to be uncoupled from the heart of patient 36, another surgical pathway is created from the incision to pulse generator 40. End 44 is uncoupled from pulse generator 40 by removing connector 52 from a socket 62 of pulse generator 40 or a socket 64 of pulse generator 40, for example. Lead 38 is then removed from the patient and discarded. After lead 38 is removed from the patient and discarded, an end of lead 96 is coupled to the patient's heart and an opposite end 102 of lead 96 is coupled to pulse generator 40.

Over time, biofilm will form on and/or around lead 96. To remove such biofilm, end 102 is uncoupled from pulse generator and is then coupled to a power source, while the opposite end of lead 96 remains coupled to the patient's heart. The power source is turned from an off position to an on position to provide energy to transducer 98 such that transducer 98 propagates ultrasound waves that move through lead 96. As the ultrasound waves move along the length of lead 96, the ultrasound waves cause lead 96 to vibrate such that biofilm on and/or around an outer surface of lead 96 is disrupted.

In some embodiments, antibiotics are simultaneously administered to the patient while the biofilm on and/or around lead 96 is disrupted by the ultrasound waves. In some embodiments, antibiotics are administered to the patient before the biofilm on and/or around lead 96 is disrupted by the ultrasound waves. That is, the antibiotics may be administered to the patient before lead 96 is uncoupled from pulse generator 40. In some embodiments, antibiotics are administered to the patient before and/or after the biofilm on and/or around lead 96 is disrupted by the ultrasound waves. In some embodiments, the antibiotics are administered systemically and/or locally. In some embodiments, lead 96 remains coupled to the patient before the surgical method is performed, while the surgical method is being performed, or after the surgical method is performed. That is, lead 96 remains coupled to the patient before lead 96 is uncoupled from pulse generator 40, while lead 96 is being coupled to the power source and while transducer 98 propagates ultrasound waves that move through lead 96.

Upon completion of a procedure, as described herein, the surgical instruments, assemblies and non-implanted components of surgical system 30 are removed and the incision(s) are closed. One or more of the components surgical system 30 can be made of radiolucent materials such as polymers. Radiomarkers may be included for identification under x-ray, fluoroscopy, CT or other imaging techniques.

In some embodiments, at least one lead 96 is implanted at the same time that device 32 is implanted in a patient, such that lead(s) will never have to be removed from the patient and/or be uncoupled from device 32. That is, lead(s) 96 is coupled to device 32 upon implantation of device 32 and will remain coupled to device 32 until device 32 is removed from the patient, if ever. Lead(s) 96 may be uncoupled from pulse generator 40 and subsequently coupled to transducer 98 periodically, such as, for example, after biofilm builds upon on lead(s) 96 over time, to propagate ultrasound waves that move through lead(s) 96 to disrupt any biofilm that has built upon lead(s) 96. Lead(s) 96 are then uncoupled from transducer 98 and are subsequently recoupled to pulse generator 40.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A surgical method for treating infections on a lead positioned at least partially within a patient's body, the surgical method comprising:
   creating an incision in the patient;
   creating a surgical pathway from the incision to the lead;
   uncoupling the lead from a pulse generator;
   coupling the lead to an ultrasound wave generator; and
   propagating ultrasound waves from the ultrasound wave generator through the lead.

2. The surgical method recited in claim 1, wherein the ultrasound waves are propagated through the lead to disrupt biofilm on the lead.

3. The surgical method recited in claim 2, further comprising administering antibiotics to the patient after the biofilm on the lead is disrupted by the ultrasound waves.

4. The surgical method recited in claim 2, further comprising systemically administering antibiotics to the patient before the biofilm on the lead is disrupted by the ultrasound waves.

5. The surgical method recited in claim 1, wherein the ultrasound waves are propagated through the lead to disrupt biofilm on the lead, the surgical method further comprising administering antibiotics to the patient before propagating ultrasound waves from the ultrasound wave generator through the lead.

6. The surgical method recited in claim 5, further comprising administering antibiotics to the patient after the biofilm on the lead is disrupted by the ultrasound waves.

7. The surgical method recited in claim 1, wherein the lead is not removed from the patient before the surgical method is performed, while the surgical method is being performed, or after the surgical method is performed.

8. The surgical method recited in claim 1, wherein coupling the lead to the ultrasound wave generator comprises coupling a first end of the lead to the ultrasound wave generator while an opposite second end of the lead is coupled to the patient's heart.

9. The surgical method recited in claim 1, wherein the ultrasound waves are propagated through an inner coil of the lead to disrupt biofilm on the lead.

10. A surgical method for treating infections on a lead comprising:
    creating an incision in a patient;
    creating a surgical pathway from the incision to a lead;
    uncoupling the lead from a pulse generator;
    coupling the lead to an ultrasound wave generator; and
    propagating ultrasound waves from the ultrasound wave generator through the lead, and
    wherein the lead is not removed from the patient before the surgical method is performed, while the surgical method is being performed, or after the surgical method is performed.

11. The surgical method recited in claim 10, wherein the ultrasound waves are propagated through the lead to disrupt biofilm on the lead.

12. The surgical method recited in claim 11, further comprising administering antibiotics to the patient after the biofilm on the lead is disrupted by the ultrasound waves.

13. The surgical method recited in claim 11, further comprising systemically administering antibiotics to the patient before the biofilm on the lead is disrupted by the ultrasound waves.

14. The surgical method recited in claim 10, wherein the ultrasound waves are propagated through the lead to disrupt biofilm on the lead, the surgical method further comprising administering antibiotics to the patient before propagating ultrasound waves from the ultrasound wave generator through the lead.

15. The surgical method recited in claim 14, further comprising administering antibiotics to the patient after the biofilm on the lead is disrupted by the ultrasound waves.

16. The surgical method recited in claim 10, wherein coupling the lead to the ultrasound wave generator comprises coupling a first end of the lead to the ultrasound wave generator while an opposite second end of the lead is coupled to the patient's heart.

17. The surgical method recited in claim 10, wherein the ultrasound waves are propagated through an inner coil of the lead to disrupt biofilm on the lead.

18. A surgical method for treating infections on a lead comprising:
    creating an incision in a patient;
    creating a surgical pathway from the incision to a lead;
    uncoupling the lead from a pulse generator;
    coupling the lead to an ultrasound wave generator; and
    propagating ultrasound waves from the ultrasound wave generator through the lead, wherein the lead is not removed from the patient before the surgical method is performed, while the surgical method is being performed, or after the surgical method is performed, and
    wherein coupling the lead to the ultrasound wave generator comprises coupling a first end of the lead to the ultrasound wave generator while an opposite second end of the lead is coupled to the patient's heart.

19. The surgical method recited in claim 18, wherein the ultrasound waves are propagated through the lead to disrupt biofilm on the lead.

* * * * *